(12) United States Patent
Johnston et al.

(10) Patent No.: US 11,241,522 B2
(45) Date of Patent: ***Feb. 8, 2022

(54) APPARATUS FOR REMOVING CHEMOTHERAPY COMPOUNDS FROM BLOOD

(71) Applicant: Delcath Systems, Inc., New York, NY (US)

(72) Inventors: Daniel S. Johnston, Trappe, PA (US); Jacques Chammas, Walpole, MA (US); William M. Appling, Granville, NY (US); Samantha J. Barton, Hudson Falls, NY (US)

(73) Assignee: Delcath Systems, Inc., New York, NY (US)

(*) Notice: Subject to any disclaimer, the term of this patent is extended or adjusted under 35 U.S.C. 154(b) by 82 days.

This patent is subject to a terminal disclaimer.

(21) Appl. No.: 16/740,166

(22) Filed: Jan. 10, 2020

(65) Prior Publication Data

US 2020/0147288 A1 May 14, 2020

Related U.S. Application Data

(60) Continuation of application No. 16/439,620, filed on Jun. 12, 2019, now Pat. No. 10,569,004, which is a
(Continued)

(51) Int. Cl.
*A61M 1/34* (2006.01)
*A61M 1/36* (2006.01)
(Continued)

(52) U.S. Cl.
CPC ............ *A61M 1/34* (2013.01); *A61M 1/3406* (2014.02); *A61M 1/3615* (2014.02);
(Continued)

(58) Field of Classification Search
None
See application file for complete search history.

(56) References Cited

U.S. PATENT DOCUMENTS

| 3,372,808 A | 3/1968 | Sabo |
| 3,522,346 A | 7/1970 | Chang |
(Continued)

FOREIGN PATENT DOCUMENTS

| CA | 1057595 | 7/1979 |
| GB | 2025385 | 1/1980 |
(Continued)

OTHER PUBLICATIONS

Extended European Search Report dated Jun. 10, 2016 in connection with EP Application No. 12847108.3.
(Continued)

*Primary Examiner* — David C Mellon
(74) *Attorney, Agent, or Firm* — Hoffman Warnick LLC; Franklin S. Abrams

(57) ABSTRACT

A filter apparatus for removing small molecule chemotherapy agents from blood is provided. The filter apparatus comprises a housing with an extraction media comprised of polymer coated carbon cores. Also provided are methods of treating a subject with cancer of an organ or region comprising administering a chemotherapeutic agent to the organ or region, collecting blood laded with chemotherapeutic agent from the isolated organ, filtering the blood laden with chemotherapeutic agent to reduce the chemotherapeutic agent in the blood and returning the blood to the subject.

20 Claims, 2 Drawing Sheets

Related U.S. Application Data division of application No. 16/127,008, filed on Sep. 10, 2018, now Pat. No. 10,369,264, which is a continuation of application No. 15/651,141, filed on Jul. 17, 2017, now Pat. No. 10,098,997, which is a continuation of application No. 13/671,549, filed on Nov. 7, 2012, now Pat. No. 9,707,331.

(60) Provisional application No. 61/556,819, filed on Nov. 7, 2011.

(51) Int. Cl.

| | | |
|---|---|---|
| *C01B 32/354* | (2017.01) | |
| *C01B 32/372* | (2017.01) | |
| *B01J 20/28* | (2006.01) | |
| *B01J 20/20* | (2006.01) | |
| *B01J 20/26* | (2006.01) | |
| *B01J 20/30* | (2006.01) | |
| *B01J 20/32* | (2006.01) | |

(52) U.S. Cl.
CPC ............ *A61M 1/3687* (2013.01); *B01J 20/20* (2013.01); *B01J 20/261* (2013.01); *B01J 20/28011* (2013.01); *B01J 20/28066* (2013.01); *B01J 20/28076* (2013.01); *B01J 20/28078* (2013.01); *B01J 20/3078* (2013.01); *B01J 20/3204* (2013.01); *B01J 20/327* (2013.01); *B01J 20/3293* (2013.01); *C01B 32/354* (2017.08); *C01B 32/372* (2017.08); *A61M 2205/3306* (2013.01); *A61M 2205/50* (2013.01); *A61M 2210/1071* (2013.01)

(56) References Cited

U.S. PATENT DOCUMENTS

| | | |
|---|---|---|
| 3,725,113 A | 4/1973 | Chang |
| 3,953,360 A | 4/1976 | Morishita et al. |
| 3,983,053 A | 9/1976 | Courtney et al. |
| 4,048,064 A | 9/1977 | Clark, III |
| 4,076,892 A | 2/1978 | Fennimore et al. |
| 4,081,402 A | 3/1978 | Levy et al. |
| 4,169,051 A | 9/1979 | Satoh et al. |
| 4,171,283 A | 10/1979 | Nakashima et al. |
| 4,221,695 A | 9/1980 | Hino et al. |
| 4,358,376 A | 11/1982 | Moriuchi et al. |
| 4,452,918 A | 6/1984 | Uchida et al. |
| 5,059,654 A | 10/1991 | Hou et al. |
| 5,069,662 A | 12/1991 | Bodden |
| 5,312,586 A | 5/1994 | Stockel |
| 5,380,594 A | 1/1995 | von Blucher et al. |
| 5,412,586 A | 5/1995 | Oldfather |
| 5,416,056 A | 5/1995 | Baker |
| 5,446,005 A | 8/1995 | Endo |
| 5,710,092 A | 1/1998 | Baker |
| 5,795,843 A | 8/1998 | Endo |
| 5,956,225 A | 9/1999 | Okuyama et al. |
| 6,316,378 B1 | 11/2001 | Giebelhausen et al. |
| 7,037,642 B2 | 5/2006 | Hei |
| 7,202,195 B2 | 4/2007 | Cannon et al. |
| 7,232,790 B2 | 6/2007 | Tanaka et al. |
| 7,256,156 B2 | 8/2007 | Axtell et al. |
| 7,309,323 B2 | 12/2007 | Gura et al. |
| 7,614,506 B2 | 11/2009 | Mitchell et al. |
| 7,614,507 B2 | 11/2009 | Mitchell et al. |
| 7,614,508 B2 | 11/2009 | Mitchell et al. |
| 7,712,613 B2 | 5/2010 | Bahm et al. |
| 7,737,083 B2 | 6/2010 | von Blucher et al. |
| 7,781,370 B2 | 8/2010 | Sonobe et al. |
| 7,922,008 B2 | 4/2011 | Bahm et al. |
| 7,923,411 B2 | 4/2011 | Tanaka et al. |
| 7,964,530 B2 | 6/2011 | Nanba et al. |
| 8,119,012 B2 | 2/2012 | Bahm et al. |
| 2003/0118823 A1 | 6/2003 | Hiltzik et al. |
| 2005/0035062 A1 | 2/2005 | Hiltzik et al. |
| 2005/0279696 A1 | 12/2005 | Bahm et al. |
| 2007/0123419 A1 | 5/2007 | Le Bec |
| 2008/0171648 A1 | 7/2008 | Von Blucher et al. |
| 2009/0258782 A1 | 10/2009 | Gogotsi et al. |
| 2010/0035058 A1 | 2/2010 | Tennison et al. |
| 2010/0038304 A1 | 2/2010 | Chen et al. |
| 2010/0316694 A1 | 12/2010 | Mousa et al. |
| 2011/0139701 A1 | 6/2011 | Pearks et al. |

FOREIGN PATENT DOCUMENTS

| | | |
|---|---|---|
| WO | 2002/059039 | 8/2002 |
| WO | 2007/037508 | 4/2007 |
| WO | 2009/079332 | 6/2009 |
| WO | 2011/056181 | 5/2011 |
| WO | 2011/070363 | 6/2011 |

OTHER PUBLICATIONS

August, David A. et al.; "Hepatic Artery Infusion of Doxorubicin with Hepatic Venous Drug Extraction"; Journal of Surgical Research; vol. 56; No. 6; Jun. 1, 1994; pp. 611-619.

International Search Report for International Application No. PCT/US2012/064002.

Tijssen et al.; "A Hemoperfusion Column Based on Activated Carbon Granules Coated with an Ultrathin Membrane of Cellulose Acetate"; Artificial Organs; vol. 3; No. 1; p. 11-14 (1979).

Andrade et al.; "Activated Carbon and Blood Perfusion: A Critical Review"; Proc. Eur. Dial. Transplant Assoc.; 9(0); pp. 290-302; (1972).

Yushin et al.; "Mesoporous carbide-derived carbon with porosity tuned for efficient adsorption of cytokines"; Biomaterials, 27(34); 5755-62; (2006).

Yushin et al.; "Mesoporous carbide-derived carbon with porosity tuned for efficient adsorption of cytokines"; From Drexel E-Repository and Archive pp. 1-22 (2006).

Yushin et al.; Biomaterials; 27(34); 5755-62; (2006); Supplemental Materials.

Tian, et al.; "Modified BET equation characterizes micropore volume and meso-/macro-pore surface areas of shales"; 2015; pp. 1-2.

Cerda-Cristerna et al.; "Hemocompatibility assessment of poly(2-dimethylamino ethylmethacrylate) (PDMAEMA)-based polymers"; Journal of Controled Release; 153(3); 269-77; (2011).

Extended European Search Report for European Application No. 19180093.7; dated Sep. 17, 2019.

APPARATUS FOR REMOVING CHEMOTHERAPY COMPOUNDS FROM BLOOD

CROSS-REFERENCE TO RELATED APPLICATIONS

This patent application is a continuation of U.S. patent application Ser. No. 16/439,620 filed Jun. 12, 2019, which is a divisional application of U.S. patent application Ser. No. 16/127,008 filed Sep. 10, 2018, now U.S. Pat. No. 10,369,264, which is a continuation of U.S. patent application Ser. No. 15/651,141 filed Jul. 17, 2017, now U.S. Pat. No. 10,098,997, which is a continuation of U.S. patent application Ser. No. 13/671,549, filed Nov. 7, 2012, now U.S. Pat. No. 9,707,331, which claims priority benefit of U.S. Provisional Patent Application Ser. No. 61/556,819 filed Nov. 7, 2011, and entitled "APPARATUS FOR REMOVING CHEMOTHERAPY COMPOUNDS FROM BLOOD." The disclosures of the aforementioned Provisional Patent Application Ser. No. 61/556,819, U.S. patent application Ser. No. 16/439,620, U.S. patent application Ser. No. 16/127,008, U.S. patent application Ser. No. 15/651,141, and U.S. patent application Ser. No. 13/671,549 are hereby incorporated by reference in their entirety.

BACKGROUND

The systemic presence of toxic chemotherapeutic agents in patients undergoing chemotherapy has been the cause of great suffering and discontinuation of potentially life extending or saving treatment. Where the cancer is located to specific organs, various approaches have been taken to limit this systemic exposure to toxic chemotherapeutic agents.

The liver is an important example because primary and metastatic liver tumors are one of the largest causes of cancer deaths in the world. Hepatocellular carcinoma, for example, is one of the most common and lethal malignancies. Curley et al., Annals of Surgical Oncology 1(5): 389-399 (1994). In addition, metastases to the liver is the most common disease progression of a variety of cancers of different origins such as colorectal adenocarcinoma, ocular melanoma, neuroendocrine tumors, and gastrointestinal sarcoma resulting in oftentimes multifocal and unresectable cancers of the liver. Pingpank et al., J. Clin. Oncol. Vol 23 (15): 3465-3474 (2005).

High doses of chemotherapy have been shown to be effective in the treatment of liver cancers. However, due to the toxicity of chemotherapeutic agents, the use of high dose therapy has been limited. To overcome problems associated with systemic exposure to chemotherapy, approaches have been taken to limit systemic exposure. A demanding surgical approach, isolated hepatic perfusion (IHP), has been used to provide high doses of chemotherapy regionally to the liver. The drawbacks to this approach include lack of repeatability for a particular patient and high mortality due to the surgery. Pingpank et al., J. Clin. Oncol. Vol 23 (15): 3465-3474 (2005).

An alternative approach of great promise has become known as chemosaturation, a technique using catheter technology to percutaneously deliver a high dose of chemotherapy to the effected organ and then removal of the blood laden with chemotherapeutic agents from the organ, filtration of the blood by extracorporeal filtration, and then return of the blood, after the chemotherapeutic agent has been removed, to the patient.

In hepatic chemosaturation therapy, for example, a percutaneous hepatic perfusion (PHP) procedure intra-arterially delivers high doses of chemotherapy (anti-cancer agents) directly into the isolated liver, saturating both the liver cells and the tumor cells. The blood from the liver is then drained through an isolation-aspiration catheter and then directed outside the body to a filter system that reduces the concentration of chemotherapeutic agent in the blood before this blood is returned to the body.

Delivering high doses of chemotherapy (anti-cancer agents) to targeted organs, detoxifying the blood using an extracorporeal circuit, and returning the blood to a patient has been described in U.S. Pat. No. 5,069,662 to Bodden.

SUMMARY

The present invention stems from the inventors realization that there remains an urgent need to reduce the systemic levels of chemotherapeutic agents in cancer treatments and maintain the quality of the blood of treated patients after external filtration. Advances in this area would significantly improve the prospects and quality of life for cancer patients. The inventors recognized that to achieve the goals of reducing, or eliminating, systemic effects of chemotherapy while targeting chemotherapy to specific organs, advances in our capacity to effectively remove toxic small molecule chemotherapeutic agents from blood were required. The present invention, in some embodiments, satisfies this urgent need by providing apparatus, systems, methods, and kits for high efficiency extracorporeal removal of small molecule chemotherapy agents from blood and blood products such as plasma while maintaining platelets, white blood cells and red blood cells in good condition. The greater efficiency of removal of chemotherapeutics reduces systemic chemotherapeutic exposure and its associated toxicities such as myelosuppression. Various embodiments of the invention are provided below.

In some embodiments, provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the carbon cores have a particle diameter of about 0.45 mm to about 1.15 mm.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the apparent density of carbon cores is about 0.19 to about 0.2.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the carbon cores have a median microporous diameter ($D_{50,micro}$) of between about 9.3 Å to about 10.5 Å.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and a median mesoporous diameter ($D_{50,meso}$) of between about 30 Å to about 156 Å.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the carbon cores have a percent of microporous pores that represents between about 18% to about 28% of the pore volume.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the carbon cores have an MBET surface area of between about 1825 $m^2/g$ to about 2058 $m^2/g$.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the carbon cores have a DFT surface area of between about 1483 $m^2/g$ to about 1778 $m^2/g$.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge and the small molecule chemotherapy agent is melphalan hydrochloride and the filter apparatus has an extraction efficiency of greater than 98% for removing melphalan hydrochloride from blood using a filter cartridge in an in vitro system where blood flow through the filter cartridge is at about 250 mL/min.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge and the small molecule chemotherapy agent is melphalan hydrochloride and the filter apparatus has an extraction efficiency of between about 95% and about 98% for removing melphalan hydrochloride from blood using a filter cartridge in an in vitro system where blood flow through the filter cartridge is at about 500 mL/min.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge and the small molecule chemotherapy agent is melphalan hydrochloride and the filter apparatus has an extraction efficiency of greater than about 95% for removing melphalan hydrochloride from blood using a filter cartridge in an in vitro system.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge and the small molecule chemotherapy agent is doxorubicin and the filter apparatus has an extraction efficiency of greater than about 95% for removing doxorubicin from blood using a filter cartridge in an in vitro system where blood flow through the filter cartridge is at about 250 mL/min.

In some embodiments provided herein is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and the housing is a filter cartridge and the small molecule chemotherapy agent is topotecan and the filter apparatus has an extraction efficiency of greater than about 89% for removing topotecan from blood using a filter cartridge in an in vitro system where blood flow through the filter cartridge is at about 250 mL/min.

In some embodiments of the filter apparatus for removing small molecule chemotherapy agents from blood, the polymer coated carbon cores are coated with a semipermeable polymer coating comprised of material selected from the group consisting of cellulose, a methacrylate polymer, and combinations thereof.

In some embodiments of the filter apparatus for removing small molecule chemotherapy agents from blood, the semipermeable polymer coating is a methacrylate selected from the group consisting of polymethylmethacrylate (PMMA), polyethylmethacrylate (PEMA), polyhydroxyethyl-methacrylate (PHEMA) and combinations thereof.

In some embodiments of the filter apparatus for removing small molecule chemotherapy agents from blood, the semipermeable polymer coating is polyhydroxyethyl-methacrylate (PHEMA).

In some embodiments of the filter apparatus for removing small molecule chemotherapy agents from blood, the weight:weight ratio of carbon to methacrylate is between 52:1 to 25:1.

In some embodiments, provided is a filter apparatus for removing small molecule chemotherapy agents from blood comprising a housing having an inlet and an outlet, an extraction media comprising polymer coated carbon cores contained within the housing, wherein the carbon cores have a pore volume of about 1.68 cc/g to about 2.17 cc/g and an MBET surface area of between about 1825 $m^2/g$ to about 2059 $m^2/g$.

In some embodiments provided is a filter apparatus for removing small molecule chemotherapy agents from blood, wherein the carbon cores have a pore volume of about 1.68 cc/g to about 2.17 cc/g, an MBET surface area of between about 1825 $m^2/g$ to about 2059 $m^2/g$ and a DFT surface area is between about 1483 $m^2/g$ and about 1778 $m^2/g$.

In some embodiments provided is a filter apparatus for removing small molecule chemotherapy agents from blood, wherein the carbon cores have a pore volume of about 1.68 cc/g to about 2.17 cc/g, an MBET surface area of between about 1825 m$^2$/g to about 2059 m$^2$/g a DFT surface area of between about 1483 m$^2$/g and about 1778 m$^2$/g, and an apparent density of between about 0.185 to about 0.195.

In some embodiments provided is a filter apparatus for removing small molecule chemotherapy agents, the small molecule chemotherapy agent is melphalan hydrochloride and the filter apparatus has an extraction efficiency of greater than 98% for removing melphalan hydrochloride from blood using a filter cartridge in an in vitro system where blood flow through the filter cartridge is at about 250 mL/min.

In some embodiments, provided is a filter apparatus for removing melphalan hydrochloride from blood comprising a housing having an inlet and an outlet, an extraction media comprising polymer coated carbon cores contained within the housing, wherein the carbon cores have an apparent density of less than 0.2 g/cc and an extraction efficiency of greater than 98% for removing melphalan hydrochloride from blood.

In some embodiments, provided is a filter apparatus for removing melphalan hydrochloride from blood comprising a housing having an inlet and an outlet, an extraction media comprising polymer coated carbon cores contained within the housing, wherein the carbon cores have an apparent density of less than 0.2 g/cc and an extraction efficiency of greater than 98% for removing melphalan hydrochloride from blood and the carbon cores have a pore volume of about 1.68 cc/g to about 2.19 cc/g.

In some embodiments, provided is a filter apparatus for removing melphalan having a concentration less than 15,000 ng/mL from blood, comprising one or more filter cartridge comprising an extraction media comprising polymer coated carbon cores contained within the filter cartridge, wherein the carbon cores have a pore volume of about 1.68 to about 2.19 cc/g and an apparent density of less than about 0.2 g/cc, and wherein the filter apparatus has an extraction efficiency for melphalan of greater than 98% when blood flows through the filter apparatus at a rate of 500 ml/L or less.

In some embodiments provided is a filter apparatus for removing melphalan having a concentration less than 15,000 ng/mL from blood, comprising one or more filter cartridge comprising an extraction media comprising polymer coated carbon cores contained within the filter cartridge, wherein the carbon cores have a pore volume of about 1.68 to about 2.19 cc/g and an apparent density of less than about 0.2 g/cc, and wherein the filter apparatus has an extraction efficiency for melphalan of greater than 98% when blood flows through the filter apparatus at a rate of 500 ml/L or less, wherein the filter apparatus comprises two filter cartridges.

In some embodiments provided is a filter apparatus for removing melphalan having a concentration less than 15,000 ng/mL from blood, comprising one or more filter cartridge comprising an extraction media comprising polymer coated carbon cores contained within the filter cartridge, wherein the carbon cores have a pore volume of about 1.68 to about 2.19 cc/g and an apparent density of less than about 0.2 g/cc, and wherein the filter apparatus has an extraction efficiency for melphalan of greater than 98% when blood flows through the filter apparatus at a rate of 500 ml/L or less wherein the two filter cartridges are parallel to each other and flow is split such that fluid passes through the two filter cartridges in parallel.

In some embodiments, provided is a method of treating a subject with cancer of the liver, comprising: isolating blood flow out of the liver; administering a chemotherapeutic agent arterially to the isolated liver; collecting blood laden with chemotherapeutic agent from the isolated liver; and filtering the blood laden with chemotherapeutic agent with a filter apparatus comprising a housing having an inlet and an outlet, an extraction media comprising polymer coated carbon cores contained within the housing, wherein the polymer coated carbon cores have an apparent density of less than 0.21 g/cc.

In some embodiments, provided is a method of treating a subject with cancer of the liver, comprising: isolating blood flow out of the liver; administering a chemotherapeutic agent arterially to the isolated liver; collecting blood laden with chemotherapeutic agent from the isolated liver; and filtering the blood laden with chemotherapeutic agent with a filter apparatus comprising a housing having an inlet and an outlet, an extraction media comprising polymer coated carbon cores contained within the housing, wherein the polymer coated carbon cores have an apparent density of less than 0.21 g/cc and wherein the chemotherapeutic agent is melphalan hydrochloride. In some embodiments an extraction efficiency of greater than 98% for removing melphalan hydrochloride from blood is achieved. In some embodiments an extraction efficiency of greater than 98% for removing melphalan hydrochloride from blood is achieved when blood flow through the filter apparatus at a rate of about 500 ml/L or less.

In some embodiments, the carbon cores have an apparent density of less than 0.21 g/cc.

In some embodiments, provided is a method of treating a subject with cancer of the liver, comprising: isolating blood flow out of the liver; administering a chemotherapeutic agent arterially to the isolated liver; collecting blood laden with chemotherapeutic agent from the isolated liver; and filtering the blood laden with chemotherapeutic agent with a filter apparatus comprising a housing having an inlet and an outlet, an extraction media comprising polymer coated carbon cores contained within the housing, wherein the polymer coated carbon cores have an apparent density of less than 0.21 g/cc and wherein the chemotherapeutic agent doxorubicin or topotecan.

In some embodiments, provided is a method of treating a subject with cancer of the liver, comprising: isolating blood flow out of the liver; administering a chemotherapeutic agent arterially to the isolated liver; collecting blood laden with chemotherapeutic agent from the isolated liver; and filtering the blood laden with chemotherapeutic agent with a filter apparatus comprising a housing having an inlet and an outlet, an extraction media comprising polymer coated carbon cores contained within the housing, wherein the polymer coated carbon cores have an apparent density of less than 0.21 g/cc and wherein the chemotherapeutic agent, wherein the filter apparatus comprises one or more filter cartridge.

In some embodiments, provided is a method of treating a subject with cancer of the liver, comprising: isolating blood flow out of the liver; administering a chemotherapeutic agent arterially to the isolated liver; collecting blood laden with chemotherapeutic agent from the isolated liver; and filtering the blood laden with chemotherapeutic agent with a filter apparatus comprising a housing having an inlet and an outlet, an extraction media comprising polymer coated carbon cores contained within the housing, wherein the carbon cores have an apparent density of less than 0.21 g/cc and wherein the chemotherapeutic agent, further comprising returning the blood to the patient after it has been filtered to reduce the amount of chemotherapeutic agent in the blood.

In some embodiments provided is a method of treating cancer of the liver in a patient in need of treatment, comprising introducing a first catheter into a femoral artery to provide access to a region of the proper hepatic artery; guiding the first catheter to within the region of the proper hepatic artery to deliver melphalan hydrochloride; inserting an isolation-aspiration catheter having two balloons, or expandable occlusion means, into the femoral vein and guiding the isolation-aspiration catheter into the inferior vena cava; the two balloons, or expandable occlusion means, are then inflated, or expanded, to block normal venous outflow of blood from the liver to the heart and isolate the liver; a dose of melphalan of from about 2.0 mg/kg to about 3.5 mg/kg of the subjects body weight is delivered to the liver via the first catheter over a period of from about 15 minutes to about 45 minutes; the melphalan-laden blood is then collected as it exits the liver in the region between the two inflated balloons, or expandable occlusion means, of the isolation-aspiration catheter and passed at a rate of between about 250 ml/min and about 1000 ml/min through a filter apparatus in accordance with some embodiments of the inventions to remove greater than 98% of melphalan hydrochloride from the blood, and returning blood that has been passed through the filter apparatus (filtered) to the patient through a third catheter placed in the internal jugular vein.

In some embodiments, the invention provides a system for delivering a high concentration of a small molecule chemotherapeutic agent to a subject in need of treatment while minimizing systemic exposure to the small molecule chemotherapeutic agent, the system comprising a catheter inserted percutaneously into the inferior vena cava of a patient in need of treatment, the catheter comprising a hemo-compatible tube having a cranial end and a caudal end, the hemo-compatible tube defining a main lumen for outflowing blood, two balloons, fixedly spaced apart about the hemo-compatible tube and bonded thereto for inflation thereabout, one being contiguous to the cranial end, and the balloons, when inflated, having a size sufficient to block the flow of blood in a vein or artery into which the first catheter is designed to be inserted; fenestrations in the hemo-compatible tube between the balloons to the main lumen; second and third lumina within the hemo-compatible tube, the second lumen connecting to one of the balloons and the third lumen connecting to the other of the balloons, or other expandable devices, for effecting inflation or deflation of the balloons, the cranial end of the hemo-compatible tube effectively blocking inflow of blood; a filter apparatus in accordance with some embodiments of the invention for removing the small molecule chemotherapeutic agents from blood, wherein the filter apparatus is capable of being connected via a connector to the first catheter and a flow machine for pumping the blood from the subject through the filter apparatus, and a sheath or return catheter for returning blood removed from the patient back to the patient after filtration.

In some embodiments the subject of the system for delivering a high concentration of a small molecule chemotherapeutic agents is a human.

In some embodiments of the invention the system for delivering a high concentration of a small molecule chemotherapeutic agent to a subject can be provided in the form of a kit of parts capable of being assembled.

In other embodiments of the invention a series of hemofiltration cartridges are used to provide a continuous source of fresh extraction media. In some embodiments of the invention the series of filters are changed during a treatment by mechanical or electronic means in a position before or after the pump in a hemofiltration circuit. In some embodiments a microprocessor is used to control the change of filters. In some embodiments, filter efficiency, or extraction efficiency, is monitored in real time and filter cartridges are switched in response to any decreases in extraction efficiency. In some embodiments of the invention a series of filter apparatus are arranged on a turntable like apparatus or other structure that moves filter cartridges.

In some embodiments, the invention provides a method for delivering a small molecule chemotherapeutic agents to a selected organ, or section of an organ, of a mammalian subject while restricting systemic exposure of the mammalian subject to the small molecule chemotherapeutic agent, comprising:
a. placing one or more catheters within the venous vasculature which drains the organ, at least one of the catheters having two or more expandable members;
b. isolating the organ, or section of the organ, by occluding flow of blood within the venous vasculature which drains the organ, or section of the organ, by inflating the expandable members;
c. delivering the chemotherapeutic agent to the isolated organ or isolated section of the organ;
d. allowing the chemotherapeutic agent to perfuse within the isolated organ for a period of time sufficient to provide a therapeutic effect;
e. removing blood from the isolated organ, the blood comprising the small molecule chemotherapeutic agent,
f. filtering the blood to remove the small molecule chemotherapeutic agent by passing the blood through a filter apparatus for removing small molecule chemotherapy agents from blood comprising a housing having an inlet and an outlet, an extraction media comprising polymer coated carbon cores contained within the housing, wherein the carbon cores have a density of between about 0.185 g/mL and about 0.195 g/mL and the filter apparatus has an extraction efficiency for the small molecule chemotherapy agents of greater than about 95%.

An important advantage of the high efficiency removal of chemotherapeutic agents provided by the filter apparatus, systems, methods, and kits of some embodiments of the invention is that they provide for reduced systemic exposure to toxic chemotherapeutic agents (cancer drugs) leading to less bone marrow suppression which in turn reduces the incidence and severity of neutropenia, thrombocytopenia and anemia resulting in patients being able to continue treatments and suffer less debilitating effects. The reduction in the frequency and severity of these conditions decreases patient discomfort, suffering and susceptibility to infection. This provides physicians with the opportunity to reinitiate treatments more rapidly than has been possible before. Reduced systemic exposure to chemotherapy agents will also reduce the frequency and severity of other known toxicities including but are not limited to nausea, vomiting, oral ulceration, hair loss, interstitial pneumonitis, infertility, rash and itching.

DETAILED DESCRIPTION OF THE INVENTION

Figure 1:
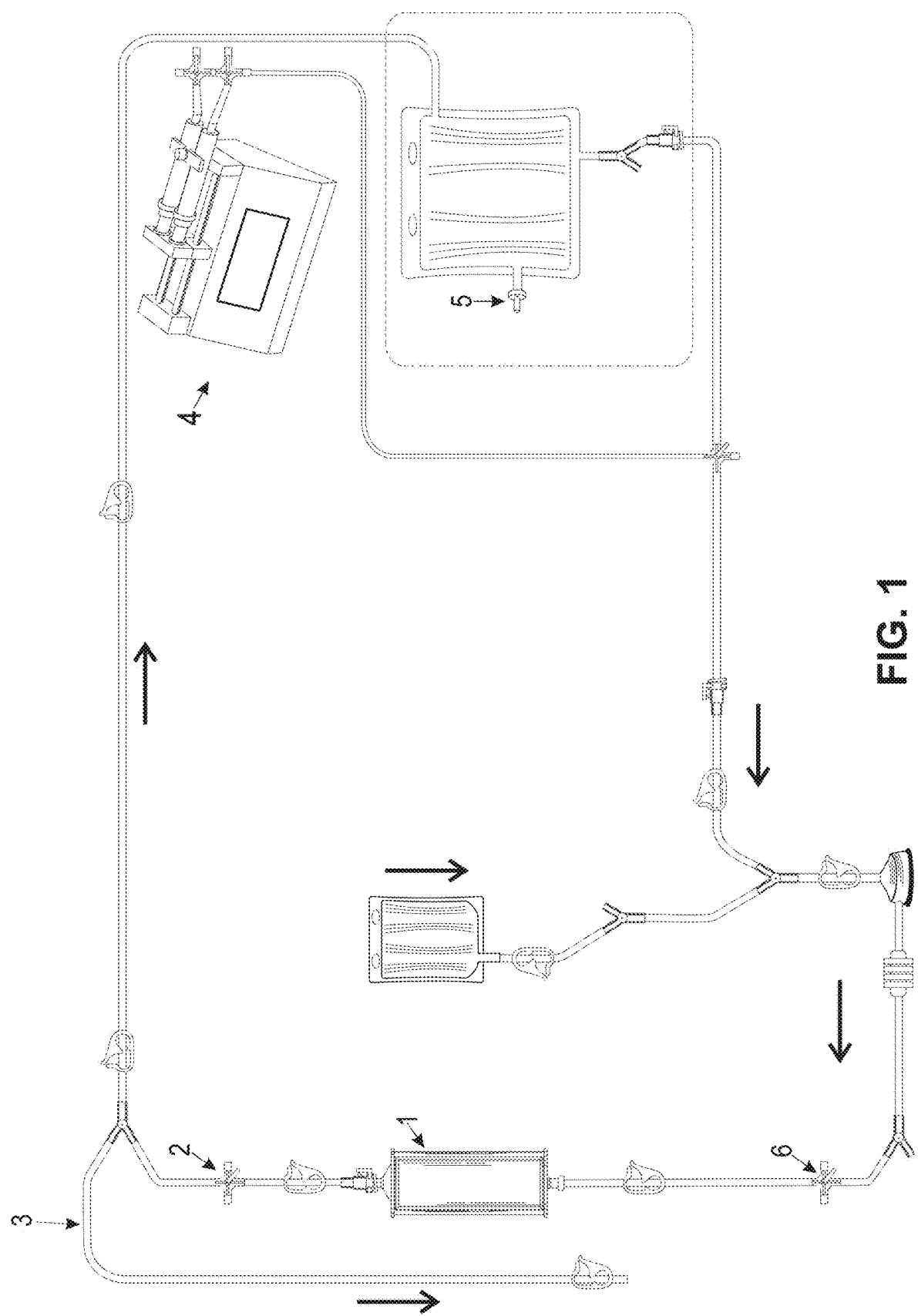
FIG. 1 shows an extracorporeal circuit as used for in vitro testing of the efficiency of filter apparatus.

The inventors have surprisingly found that a filter apparatus comprising a polymer coated low density activated carbon cores and systems, methods, and kits that use this filter apparatus can reduce the concentration of low molecular weight chemotherapeutic agents (chemotherapy drugs), in some embodiments, at an efficiency greater than 98%. While in preferred embodiments the invention is useful for removing small molecule chemotherapeutic agents from blood, some embodiments of the invention can be used to remove other toxic small molecule organic compounds from blood or other body fluids.

In some embodiments the invention is particularly useful in percutaneous techniques wherein specific organs have been isolated. An important embodiment of the invention, because of the urgent need for new approaches to treat primary and metastatic liver cancer, is to use the filter apparatus of the invention as part of a percutaneous hepatic perfusion system to deliver high dose chemotherapy to the liver while greatly reducing systemic exposure to the chemotherapy. The filter apparatus as described herein, in some embodiments of the invention, can be part of systems for percutaneous organ isolation and cancer treatment as described, for example, in U.S. Pat. Nos. 5,069,662 and 5,411,479, both to Bodden, which are herein incorporated by reference. In U.S. Pat. Nos. 5,069,662 and 5,411,479, as here, an important application is that of percutaneous hepatic perfusion.

In accordance with some embodiments of the invention high concentrations of small molecule chemotherapy (anti-cancer agents) can be perfused through a body organ containing a tumor and then removed from the organ with effluent blood. The blood contaminated with small molecule chemotherapy can then be transported to an extracorporeal circuit comprising the filter apparatus described herein and the small molecule chemotherapy is removed from the blood with greater than 98% efficiency and the purified blood is then returned to the body thereby providing for infusion of much greater than usual doses of small molecule chemotherapy to the tumors while preventing toxic levels of the small molecule chemotherapy from entering the systemic system of the patient.

As used herein, "a" and "an" can mean one or more as is commonly understood in patent claim construction.

As used herein "small molecule chemotherapy agents" refer to organic compounds in the molecular weight range of about 200 to 1500 that are useful as chemotherapy agents. Chemotherapy agents are drugs that are used to treat cancer in all forms. The terms chemotherapeutic agents, anti-cancer agents, chemotherapy, are all used interchangeably herein.

In some embodiments, the filtration apparatus of the invention is used to remove small molecule chemotherapy agents from the blood of patients undergoing chemotherapy targeted to cancers present in specific organs, glands or regions that can be isolated. For example, cancerous organs such as the liver, kidney, pancreas, and bladder, glands such as the adrenals, pancreas, prostate, thyroid and parathyroid, and the pelvic region are encompassed within the scope of the invention. For example, in some embodiments, the invention comprises a system, including the filter apparatus, for isolation and treatment of cancers of the liver. However, embodiments of the present invention find application with treatment of cancer with small molecule chemotherapy agents in any discrete isolatable region of the body.

In some embodiments, hypoxic abdominal perfusion (HAP) is used to isolate all or part of the abdominal cavity and before delivering chemotherapeutic agent(s) to treat this cancers present in this region. In some embodiments, intraperitoneal hyperthermic chemotherapy (IPHC) is used to isolate the peritoneal cavity before administering chemotherapeutic agent(s) to these regions. melphalan, paclitaxel or combinations thereof to treat primary colorectal cancer. In some embodiments of the inventions, blood from these isolated regions is filtered after chemotherapy treatment using the apparatus disclosed herein in its various embodiments.

Small molecule chemotherapy agents (anti-cancer agents) that can be removed from blood in some embodiments of the invention include melphalan hydrochloride (also known by persons of skill in the art as melphalan, Alkaran, L-phenylalanine mustard, phenylalanine mustard, L-PAM, or L-sarcolysin), doxorubicin (also known as Adriamycin). Although not an exclusive list, other small molecule chemotherapy agents that can be removed from blood with some embodiments of the invention include doxorubicin (Adriamycin), fluorinated pyrimidines (5-fluorouracyl 5-FU or floxuridine FURD), cisplatin, oxaliplatin, topotecan. Mytomycin C, cyclophosphamide, methotrexate, vincristine, Bleomycin, FAMT, and any other small molecule anti-cancer agents. Blood detoxification can, for example, be achieved by hemoperfusion through a filter cartridge incorporating the filter apparatus described herein and in accordance with some embodiments of the invention.

The coating that surrounds the carbon cores in some embodiments is comprised of poly(2-hydroxyethyl methacrylate). The thickness of the coating that covers the particles is determined largely by the mass ratio of carbon cores to poly(2-hydroxyethyl methacrylate) used in the coating process. In preparing the polymer cores the poly(2-hydroxyethyl methacrylate) is dissolved in ethanol and the carbon cores were soaked in the solution until dry, leaving a poly(2-hydroxyethyl methacrylate) coating on the particles. Weight:Weight ratios of carbon:poly(2-hydroxyethyl methacrylate ranging from 52:1 to 25:1 were tested and the extraction efficiencies during in vitro testing were found to be statistically equivalent. In some embodiments of the invention the weight: weight ratios of carbon cores to poly(2-hydroxyethyl methacrylate are between 52:1 and 25:1. In other embodiments of the invention, the weight to weight ration of carbon cores to poly(2-hydroxyethyl methacrylate is about 25:1 (a 4% poly(2-hydroxyethyl methacrylate).

In some embodiments of the invention the small molecule chemotherapy agents are selected from melphalan, doxorubicin (also known as hydroxydaunorubicin and sold under the brand names Adriamycin, Adriamycin PFS, Adriamycin RDF, or Rubex), Docetaxel, paclitaxel, fluorinated pyrimidines (5-fluorouracyl 5-FU or floxuridine FURD), cisplatin, oxaliplatin, topotecan. Mytomycin C, cyclophosphamide, methotrexate, vincristine, Bleomycin, FAMT, pharmaceutically acceptable salts thereof, combinations thereof, and other such compounds known to persons of skill in the art.

In some embodiments, pharmaceutically acceptable salts of any of the chemotherapeutic agents disclosed herein are used. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of melphalan, paclitaxel, and oxaliplatin can be prepared from an inorganic acid or from an organic acid. Inorganic acids include, for example, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound In some embodiments, the chemotherapeutic agent is melphalan. Melphalan is marketed under the trade name Alkeran by GlaxoSmithKline, is a cytotoxic and alkylating agent used in cancer chemotherapy. It is a phenyalanine derivative of nitrogen mustard, and is also referred to as L-phenylalanine mustard (L-PAM), phenyalanine mustard, or L-sarcolysin. The IUPAC systematic name is 4-[bis)2-chloroethyl) amino]-L-phenylalanine.

In some embodiments doxorubicin hydrochloride, also known as hydroxydaunorubicin is used and sold and marketed under the tradenames, Adriamycin PFS, Adriamycin RDF, or Rubex.

The filter apparatus, methods, and systems described herein can also be used for detoxification of the blood of patients having a variety of small molecule poisons such as those associated with various non-therapeutic drugs, therapeutic drugs, and kidney failure.

As used herein "blood" can be blood as it is ordinarily found within a mammalian subject, such as a human, but the term, as used herein, can also refer to other blood products such as plasma.

As used herein in reference to the filter apparatus "housing" refers to a hemo-compatible and biocompatible structure with an inlet and an outlet that is used to contain the extraction media. In some embodiments the housing can be a cylindrical structure with an inlet and an outlet.

As used herein, "filter cartridge" refers to a cylindrical column having a length of about 7.8 inches between screens at the ends of the column that are used to contain filter media and a diameter of about 2.4 inches, having an inlet and an outlet, comprised of a hemocompatible thermoplastic material, and containing about 101 to 111 grams of filter media (extraction media), the filter media having a bulk volume range of about 535 mL to about 544 mL.

Thermoplastic material, as used herein, refers to polysulfone, polycarbonate, polyacrylic, polyurethane, and the like, as understood by persons skilled in the art. Generally, polymers that provide rigid structures that are hemocompatible can be used in embodiments described herein. In some embodiments, the thermoplastic material is transparent. In some embodiments the thermoplastic material is a polysulfone.

As used herein, "polymer coating" refers to a semi-porous polymer that coats the activated carbon particles used in the present invention and renders them hemocompatible. Suitable polymers that can be used for this purpose include cellulose and polymers of methacrylate. For example, in some embodiments of the invention polymethylmethacrylate (PMMA), polyethylmethacrylate (PEMA), polyhydroxyethyl-methacrylate (PHEMA) and combinations thereof can be used. While not exhaustive, other polymers that can be used in some embodiments of the invention include poly(N-vinylpyrrolidinone), poly(hydroxyethyl acrylate), hydroxyethyl cellulose, hydroxypropyl cellulose, salts of poly(acrylic acid), salts of poly(methacrylic acid), poly(dimethylaminoethyl methacrylate), poly(dimethylaminoethyl acrylate), poly(diethylaminoethyl acrylate), poly (diethylaminoethyl methacrylate), poly(vinyl alcohol), and the like.

Monomer starting materials that can be used for formation of the polymer coating in some embodiments of the invention include, for example, acrylic or (meth)acrylic acid derivatives including dimethylaminoethyl (meth)acrylate, diethylaminoethyl (meth)acrylate, dimethylaminopropyl (meth)acrylate, 3-dimethylamino-2-hydroxypropyl (meth)acrylate), acrylamide or methacrylamide derivative. In addition acrylamide and methacrylamide such as N-dimethylaminoethyl (meth)acrylamide, N-diethylaminoethyl (meth) acrylamide can be used. Vinyl derivatives of such nitrogen containing compounds such as 2-vinylpyridine, 4-vinylpyridine, 2-methyl-5-vinylpyridine, 4-vinylimidazole, N-vinyl-2-ethylimidazole, vinylpyrrolidinone, N-vinyl-2-methylimidazole, can also be used in some embodiments of the invention. Combinations of monomers are also of use in some embodiments of the invention to form a variety of copolymers that persons of skill in the art would understand would impart properties in accordance with some embodiments of the invention.

In some embodiments the polymer coated carbon cores have an apparent density of between about 0.19 g/cc and 0.21 g/cc.

As used herein "density" or "apparent density" refers to the mass of a population of carbon cores divided by the total volume they occupy. The terms "density" and "apparent density" are used herein interchangeably.

As used herein "extraction efficiency" refers to the results of the following calculation for a single pass through a filter in accordance with the following calculation: Extraction Efficiency=(Pre Filter Concentration−Post Filter Concentration/Pre Filter Concentration)×100

EXAMPLES

Materials

The coating material used in the examples, Poly (2-Hydroxyethyl Methacrylate), was purchased from Sigma Aldrich in powder form and is also referred to herein as poly(2-HEMA) or poly-HEMA; Melphalen (Alkeran®) (2-amino-3-[4-[bis(2-chloroethyl)amino]phenyl]-propanoic acid) was purchased from BioNiche for animal studies and Sigma Aldrich for in vitro experiments; Other chemicals, unless noted otherwise, were purchased from Sigma Aldrich.) Hydrochloric Acid, 37%, Methanol≥99.8%, Sigma Aldrich Bovine Blood and sodium heparin were purchased from Lampire (Pipersville, Pa.). Heparain was added before each run (1000 units/L).

Example 1

Preparation of Polymer Coated Carbon Cores (Activated Carbon Media or Filter Media)

This example describes how to prepare polymer coated activated carbon particles as used in the extraction media. Activated carbon or carbon can be purchased from commercial sources, for example Siemens or Rohm & Haas, or prepared in accordance with methods known in the art, see for example, U.S. Pat. Nos. 3,909,449; 4,273,675; and 5,236,688 which are herein incorporated by reference. There is an extensive literature on activated carbon characterization and preparation. See for example "Active Carbon" by Bansal, R. C., Donnet, J. G., and Stoeckli, H. F., Marcel Dekker, New York, 1988, which is herein incorporated by reference. Activated carbon beads as starting materials were purchased but could also be prepared by blending petroleum pitch or coal pitch with a viscosity-adjusting agent, melt molding the blend into spheres, extracting the agent by a solvent from the spheres and infusibilizing the extract in accordance with practices well known to persons of skill in the art.

A further pyrolysis (carbonization) process was then used to tailor the activated carbon particles to provide the properties effective in producing the extraction media of the present invention. In the pyrolysis step a smoldering of the starting material was at high temperatures, usually above 500° C., and preferably above 800° C.

The additional pyrolysis was carried out under conditions understood by persons skilled in the art to create conditions of carbon decomposition that provide pores and optimal surface area. The carbon decomposition under high temperatures and varying the atmosphere from batch to batch selectively burns off regions of carbon providing the surface area, pore size, and density appropriate for the application of the present invention. Using this selective degradation, or oxidation, of the activated carbon starting product and then testing in the filter apparatus of the present invention for absorbance capacity of small molecule chemotherapeutic agents, activated carbon cores (hereinafter "carbon cores") were prepared.

The activated carbon cores (carbon cores) were then coated with a polymer coating that confers hemocompatibility. In the coating process, about 9.0 grams of Poly-HEMA (Poly (2-Hydroxyethyl Methacrylate)) was slowly added to about 1800 ml ethanol while stirring at a temperature of between about 60° C. and 80° C. for at least about 2 hours until the poly-HEMA was dissolved producing a uniformly clear solution of poly-HEMA. The about 1800 ml of clear poly-HEMA solution was then poured into around 1200 ml of dry activated carbon cores and the mixture was shaken for at least 27 hours until the product was free of liquid. The activated carbon cores were then dried by heating in an oven at about 90° C. for at least 24 hours.

Example 2

Characterization of Carbon Cores

The Carbon Cores were characterized using a Quantachrome®ASiQwin™ (Autosorb IQ instrument) (Quantachrome Instruments), a Camsizer® (Retsch® Technology) and by weight.

For the Quantachrome®ASiQwin™, samples were placed in a clean and dry sample cell and degassed at 300° C. for about 5 hours under vacuum. Samples were analyzed using nitrogen gas at about 77 K. Nitrogen was introduced under vacuum beginning at a partial pressure of 1.0e-7, and incrementally increasing to about 0.995 giving an adsorption curve. Nitrogen gas was then removed slowly until a partial pressure of 0.10 was achieved, resulting in a desorption curve. The surface area was then analyzed using the Multi-point BET (MBET) method and the Quenched Solid Density Functional Theory (QSDFT) method for slit/cylindrical pores with nitrogen at 77K to provide MBET and DFT surface areas. These methods are known in the art, see, for example, "Characterization of Porous Solids and Powders: Surface Area, Pore Size and Density," Lowell et al. (Springer, 2006). Autosorb iQ software was used to make the calculations using the adsorption and desorption curves. The Multi-point BET surface area was analyzed for partial pressures between 0.005-0.200.

Density Functional Theory (DFT) is known in the art and is a molecular-based statistical thermodynamic theory that relates the adsorption isotherm to the microscopic properties of the system. The DFT method provides information on pore volume and surface area as a function of half pore width whereas the MBET method provides total surface area.

As used herein, "micropores" are pores with half-pore widths (or diameter, D) less than 20 Angstroms (Å).

As used herein, "mesopores" are pores with half-pore widths greater than 20 Å and less than 250 Å.

As used herein, "the median diameter ($D_{50}$)", refers to the diameter at which 50% of the sample pore volume is below the stated pore size, and 50% of the sample pore volume is above the stated pore size. As used herein, "$D_{50,micro}$" refers to the median pore diameter in the microporous range.

As used herein "$D_{50,meso}$" refers to the median pore diameter in the mesoporous range.

As used herein the term "% Microporous Pores" refers to the percentage of the pore volume occupied by micropores.

The carbon core diameter and solid density were measured according to manufacturer instructions using a CAMSIZER®-L Digital Image Processing Particle Size and Shape Analyzer. (Retsch® Technology) The results are shown in Table 1 below.

TABLE 1

Carbon Core Measurements

| Parameter | Determined By | Average | Range |
| --- | --- | --- | --- |
| Apparent Density (g/cc) | Weighing | 0.188 | 0.185-0.195 |
| MBET Surface area (m2/g) | Quantachrome | 1946 | 1825-2058 |
| DFT Surface area (m2/g) | Quantachrome | 1644 | 1483-1778 |
| Pore Volume (cc/g) | Quantachrome | 2.03 | 1.68-2.19 |
| Pore Size Range (Å) | Quantachrome | | |
| Median Microporous Diameter, $D_{50}$, micro (Å) | | 9.7 | 9.3-10.5 |
| Median Mesoporous Diameter, $D_{50}$, meso (Å) | | 105 | 30-156 |
| Percent Microporous Pores (%) | Quantachrome | 22.37 | 18-28 |
| Particle Diameter (mm) | Camsizer | 0.73 | 0.45-1.15 |

Example 3

Extraction Efficiency

Filter Cartridges Used in Extraction Efficiency and Animal Studies

A filter cartridge (cylindrical column) with a length of about 7.8 inches between the screens used to contain filter media and a diameter of about 2.4 inches made of a thermoplastic material were filed with about 101 to 111 grams of filter media having a bulk volume range of about 535 mL to about 544 mL were used. In some examples a single filter cartridge is used. In some examples two filter cartridges are used at the same time. Unless indicated to be two cartridges, the data are referring to the use of a single filter cartridge.

Example 3A

In Vitro Extraction Efficiency

The purpose of this example is to demonstrate the filter apparatus capacity to extract a low molecular weight chemotherapeutic agent from blood. Extraction efficiency was determined for using the extracorporeal circuit shown in FIG. 1.

In FIG. 1, a schematic of in vitro experimental circuit is shown. In FIG. 1, the various elements of the experimental circuit are illustrated as would be understood by persons of skill in the art. An apparatus for removing small molecule chemotherapy agents from blood is shown 1. In FIG. 1, 2 indicates the sample port for obtaining a post-filter blood sample, 3 indicates the waste line used for removing saline from the circuit, 4 indicates the infusion pump for delivering the chemotherapeutic agent, 5 is a bag sample port, 6 is a sample port for obtaining a pre-filter blood sample.

Experimental Preparation

Bags were filled with approximately 2.5 L of blood and warmed to a minimum of 37° C. The blood was heparinized (1000 U/L) and the bags were suspended in an incubator set at approximately 50° C.

The filter was primed and completely debubbled using normal saline.

The Delcath extracorporeal tubing pack was prepared according to the following schematic.

Chemotherapeutic Preparation:

Melphalan Hydrochloride (HCl) was dissolved in a methanol and hydrochloric acid solution. The solution was then diluted with 0.9% saline.

Doxorubicin HCl was dissolved in 0.9% saline.

Topotecan was dissolved in dimethyl sulfoxide (DMSO) and then diluted with 0.9% saline.

Experimental Procedure

Syringes were filed with the chemotherapeutic solution and then attached to the extracorporeal tubing through a two, one-way stop-cock circuit meeting a ⅛" female luer adapted to a two-way stop-cock within the extracorporeal circuit. An initial blood sample was obtained for a baseline chemotherapeutic concentration value. Blood was then run through the circuit, and fluid was directed through a waste line until all visible saline was removed from the system. The waste line was clamped off and the clamp on the circuit was released, forming the complete circuit. Chemotherapeutic was then infused into the circuit via a syringe pump over 30 minutes.

Pre- and post-filter samples as well as samples from the blood bag were collected at defined intervals throughout the procedure.

All samples were immediately placed on ice for less than 20 minutes and centrifuged at 6,000 RPM for 10 minutes in a 4° C. refrigerated centrifuge. Samples were returned to ice after centrifugation and the supernatant was transferred into microcentrifuge tubes. Samples were later analyzed by liquid chromatography tandem mass spectrometry for chemotherapeutic concentration.

Sample Evaluation

All plasma samples were analyzed for the concentration of chemotherapeutic via liquid chromatography tandem mass spectrometry.

Extraction efficiency at each time point was calculated using the following equation:

Extraction Efficiency=(Pre Filter Concentration−Post Filter Concentration/Pre Filter Concentration)×100

The mean extraction efficiency at each time point was used to determine the overall efficiency for the individual experiment. The efficiency reported for an experimental group is the mean efficiency of the experiments within that group.

The Table 2 depicts the experimental results from several in vitro studies utilizing bovine blood and Table 3 shows the experimental results from an in vitro study using human blood with melphalan hydrochloride.

TABLE 2

Summary of in vitro experiments with bovine blood

| | | | Variables | | | |
|---|---|---|---|---|---|---|
| | | | Flow | Hydrogel | | |
| | | Sam- | Rate per | Ratio (g | Efficiency (%) | |
| Chemo- | Dose | ple | cartridge | media/g | | |
| therapeutic | (mg) | Size | (ml/min) | hydrogel) | Average | Range |
| Melphalan HCl | 110 | 6 | 250 | 25:1 | 99.1 | 98.5-99.7 |
| Melphalan HCl | 110 | 36 | 500 | 25:1 | 97.2 | 95.0-98.5 |
| Doxorubicin HCl | 150 | 5 | 400 | 25:1 | 95.4 | 93.4-96.8 |
| Doxorubicin HCl | 90 | 2 | 250 | 25:1 | 96.4 | 95.9-97.0 |
| Doxorubicin HCl | 150 | 2 | 400 | 25:1 | 96.9 | 96.9-96.9 |
| Topotecan | 6.25 12.5 18.75 | 3 | 250 | 25:1 | 90.3 | 89.4-91.2 |
| Topotecan | 6.25 12.5 18.75 | 3 | 500 | 25:1 | 84.3 | 84.0-85.0 |

TABLE 3

Summary of in vitro experiment with human blood and melphalan hydrochloride

| | | | Variables | | | |
|---|---|---|---|---|---|---|
| | | | Flow | Hydrogel | | |
| | | | Rate per | Ratio (g | Efficiency (%) | |
| Chemo- | Dose | Sample | cartridge | media/g | | |
| therapeutic | (mg) | Size | (ml/min) | hydrogel) | Average | Range |
| Melphalan HCl | 110 | 4 | 250 | 25:1 | 99.4 | 99.2-99.5 |
| Melphalan HCl | 110 | 3 | 500 | 25:1 | 96.7 | 96.3-97.2 |

Example 3B

In vivo Extraction Efficiency

This example demonstrates the chemotherapeutic extraction efficiencies achieved in a porcine model of chemosaturation with percutaneous hepatic perfusion (CS-PHP) with two filter cartridges arranged in parallel.

Animals and Pre-Operative Care

Yorkshire Cross pigs (4-6 months, approximately 158-216 lbs) were used in four acute studies. Food was withheld approximately 12-24 hours before surgery.

General anesthesia was induced and a cuffed endotracheal tube was inserted. An IV catheter was placed for fluid and drug administration. General anesthesia was maintained with Isoflurane delivered in oxygen through an anesthesia unit. A ventilator was used to assist respiration.

Surgical Procedure

Figure 2:
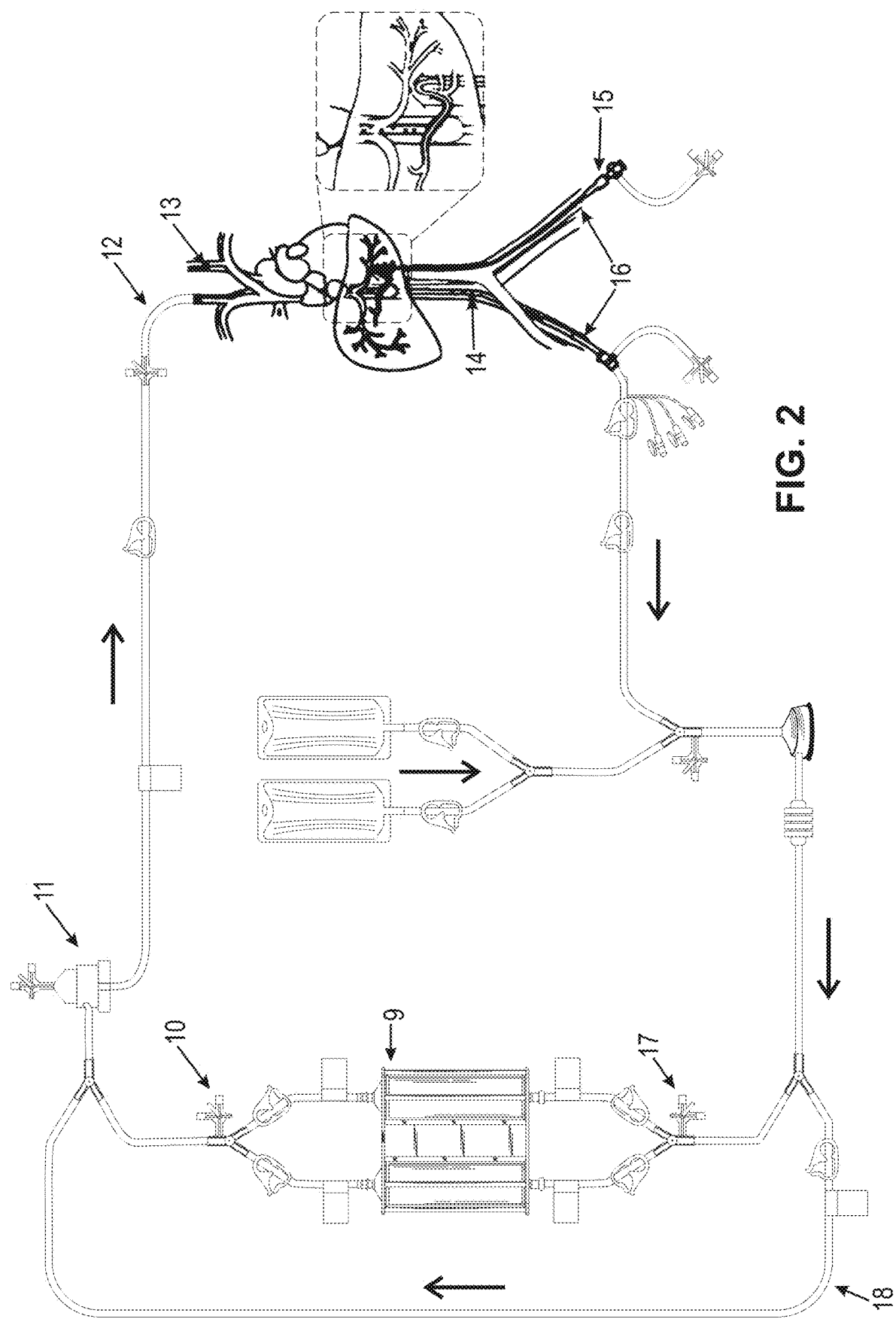
FIG. 2 shows a system for carrying out chemosaturation with percutaneous hepatic perfusion.

An experimental porcine model of percutaneous hepatic perfusion was used. A schematic representation of the CS-PHP system with experimental sample ports and pressure monitoring sites included is shown in FIG. 2. FIG. 2 shows a system according to some embodiments of the present invention for chemosaturation with percutaneous hepatic perfusion is shown. The various elements are understood by persons of skill in the art. In FIG. 2, 9 shows two filter apparatus arranged in parallel for removing small molecule chemotherapy agents from blood, 10 shows a sample port for obtaining post-filter blood samples, 11 shows an atrial filter, or bubble trap for reducing the risk of air bubbles entering the systemic circulation, 12 shows a systemic venous return sheath placed in the internal jugular vein, 13 shows a sampling port placed in the carotid artery, 14 a double balloon catheter placed in the inferior vena cava such as the one used in Delcath's Chemosat® system, shows a hepatic arterial Infusion Catheter for chemotherapeutic administration, 16 shows introducer sheaths in the femoral vein and femoral artery, 17 shows a sample port for obtaining pre-filter blood samples and 18 shows a filter bypass.

Using standard cut down techniques or percutaneous placement, an introducer sheath was placed in the femoral vein (for insertion of the double balloon catheter), femoral artery (for insertion of the hepatic arterial delivery catheter and monitoring of invasive blood pressure), jugular vein (for blood return) and carotid artery (for systemic blood sampling). Once the sheaths were placed, heparin (~300 IU/kg) was administered. Coagulation was assessed by activated clotting time (ACT), with a target ACT≥300 seconds. ACT was monitored throughout the procedure and additional heparin was administered as needed.

Using fluoroscopic guidance, the hepatic arterial catheter was placed beyond the gastroduodenal artery in preparation to deliver the chemotherapeutic agent. Under fluoroscopic guidance, the double balloon catheter was advanced over a guide wire into the inferior vena cava, and the tip positioned at the level of the diaphragmatic hiatus. The venous catheter was connected to the hemofiltration circuit and the venous return sheath was connected to the perfusion adapter. The entire system was purged of air.

Once the hemofiltration circuit was established, venous blood was aspirated from the central lumen through the fenestration in the double balloon catheter. The blood flowed through the double balloon catheter to the pump, through the filter, and returned to the animal via the venous return sheath.

The two balloons in the double balloon catheter were inflated with dilute contrast media prior to drug infusion. The cephalad balloon occluded the inferior vena cava above the highest hepatic vein and the caudal balloon occluded the inferior vena cava below the lowest hepatic vein. The hemofiltration system was brought online. Once the hemofiltration circuit was running satisfactorily administration of the chemotherapeutic agent began.

In some studies, phenylephrine was administered throughout the course of the procedure, as needed, to maintain mean arterial pressure. Boluses of sodium bicarbonate may have been administered to maintain pH at an acceptable level. Dextrose saline (5%) may have been administered intravenously in addition to normal saline throughout the procedure.

The chemotherapeutic agent was administered through the hepatic arterial catheter over a 30-minute "infusion period" Following the infusion of drug, a 30-minute "washout period" was performed where extracorporeal filtration was continued.

At the end of the procedure, blood flow to the filter cartridges was stopped one at a time by closing the appropriate attached clamps on the circuit tubing. The IsoFuse caudal balloon was then deflated followed by the deflation of the cephalad balloon. All catheters were removed from the animal and the animal was euthanized while under general anesthesia.

Sample Collection

Plasma samples were generated from blood collected at ports within the extracorporeal circuit before and after the arterial filter to determine the chemotherapeutic removal efficiency of the filter. Plasma samples generated from systemic blood were used to determine the total systemic dose that the animals received.

An initial systemic plasma sample was generated from blood drawn from the internal carotid artery immediately before the initiation of chemotherapeutic infusion to obtain a baseline systemic PK.

During the infusion and post infusion periods, pre-filter, post-filter, and systemic plasma samples were generated from blood drawn at defined intervals, starting at the beginning of infusion until the end of the washout period.

Once each blood sample was drawn they were immediately placed on wet ice. Samples were centrifuged at approximately 3600 RCF for approximately 10 minutes at approximately 4° C. and placed on wet ice until further processing. Plasma from each sample was aliquoted into a microcentrifuge tube. Plasma samples were stored at −80° C. within two hours of the initial blood draw.

Sample Evaluation

Plasma samples were analyzed for the concentration of chemotherapeutic via liquid chromatography tandem mass spectrometry.

Extraction efficiency at each time point was calculated using the following equation:

$$\text{Extraction Efficiency} = (\text{Pre Filter Concentration} - \text{Post Filter Concentration}/\text{Pre Filter Concentration}) \times 100$$

The mean extraction efficiency at each time point was used to determine the overall efficiency for the individual animals. The efficiency reported for a study is mean efficiency of the animals within that study.

Table 4 is a summary of parameters in each porcine animal study and resulting extraction efficiencies from the 60 minutes of hemofiltration.

TABLE 4

Summary of Animal Studies

| Study | 1 | 2 | 3 | 4 |
|---|---|---|---|---|
| Sample Size | 6 | 5 | 10 | 5 |
| Chemotherapeutic | Melphalan HCl | Melphalan HCl | Melphalan HCl | Doxorubicin HCl |
| Dose (mg) | 220 | 209 | 220 | 152 |
| Procedure Length (min) | | | | |
| Infusion Period | 30 | 30 | 30 | 30 |
| Washout Period | 30 | 30 | 30 | 30 |
| Overall | 60 | 60 | 60 | 60 |
| Phenylephrine (Yes or No) | No | Yes | Yes | Yes |
| Bicarbonate (Yes or No) | No | Yes | Yes | Yes |
| Dextrose (5%) Saline (Yes or No) | No | No | No | Yes |
| Animal Weight Range (lbs) | 206-216 | 158-209 | 169-209 | 158-180 |
| Target Flow Rate (mL/min) | 500 | 500 | 500 | 500 |
| Hydrogel Ratio (g media/g hydrogel) | 25 | 25 | 25 | 25 |
| Sampling Interval (min) | 3 | 6 | 6 | 5 |
| Chemotherapeutic Removal Efficiency (%) | 98.5 ± 0.5 | 96.3 ± 0.3 | 97.5 ± 0.5 | 71.4 ± 5.1 |
| Average ± Standard Deviation Range | 97.8-99.1 | 96.0-96.7 | 96.4-98.2 | 65.4-79.2 |

What is claimed is:

1. A filter apparatus comprising a housing having an inlet and an outlet, and an extraction media comprising hemocompatible polymer coated carbon cores contained within the housing, wherein the carbon cores have a pore volume of about 1.68 cc/g to about 2.19 cc/g.

2. A filter apparatus according to claim 1, wherein the carbon cores have a particle diameter of about 0.45 mm to about 1.15 mm.

3. A filter apparatus according to claim 1, wherein the carbon cores have an apparent density of about 0.19 g/cc to about 0.2 g/cc.

4. A filter apparatus according to claim 1, wherein the carbon cores have an apparent density of less than 0.2 g/cc.

5. A filter apparatus according to claim 1, wherein the carbon cores have a median microporous diameter ($D_{50,micro}$) of between about 9.3 Å to about 10.5 Å.

6. A filter apparatus according to claim 1, wherein the carbon cores have a median mesoporous diameter ($D_{50,meso}$) of between about 30 Å to about 156 Å.

7. A filter apparatus according to claim 1, wherein the hemocompatible polymer coated carbon cores contained within the housing are coated with a semipermeable polymer, the semipermeable polymer comprised of material selected from the group consisting of cellulose, a methacrylate polymer, and combinations thereof.

8. A filter apparatus according to claim 7, wherein the semipermeable polymer coating is a methacrylate selected from the group consisting of polymethylmethacrylate (PMMA), polyethylmethacrylate (PEMA), polyhydroxyethyl-methacrylate (PHEMA) and combinations thereof.

9. A dual filter apparatus for removing small molecule chemotherapy agents from blood comprising:
two filter apparatus arranged for fluid to flow through the two filter apparatus in parallel,
wherein each filter of the two filter apparatus comprises a housing having an inlet and an outlet and an extraction media comprising hemocompatible polymer coated carbon cores contained within the housing, wherein the carbon cores have a pore volume of about 1.68 cc/g to about 2.19 cc/g.

10. A dual filter apparatus according to claim 9, wherein the carbon cores have a particle diameter of about 0.45 mm to about 1.15 mm.

11. A dual filter apparatus according to claim 9, wherein the carbon cores have an apparent density of about 0.19 g/cc to about 0.2 g/cc.

12. A dual filter apparatus according to claim 9, wherein the carbon cores have an apparent density of less than 0.2 g/cc.

13. A dual filter apparatus according to claim 9, wherein the hemocompatible polymer coated carbon cores contained within the housing are coated with a semipermeable polymer, the semipermeable polymer comprised of material selected from the group consisting of cellulose, a methacrylate polymer, and combinations thereof.

14. A filter apparatus according to claim 13, wherein the semipermeable polymer coating is a methacrylate selected from the group consisting of polymethylmethacrylate (PMMA), polyethylmethacrylate (PEMA), polyhydroxyethyl-methacrylate (PHEMA) and combinations thereof.

15. A dual filter apparatus according to claim 9, wherein the chemotherapy agent is melphalan hydrochloride.

16. A dual filter apparatus according to claim 15, wherein an extraction efficiency of greater than 95% for removing melphalan hydrochloride from blood is achieved when blood flows through the dual filter apparatus at a rate of 250 ml/L or less.

17. A dual filter apparatus for removing small molecule chemotherapy agents from blood comprising:
two filter apparatus arranged for fluid to flow through the two filter apparatus in parallel,
wherein each filter of the two filter apparatus comprises a housing having an inlet and an outlet and an extraction media comprising hemocompatible polymer coated carbon cores contained within the housing, wherein the polymer coated carbon cores have an apparent density of less than 0.2 g/cc.

18. A dual filter apparatus according to claim 17, wherein the carbon cores have a pore volume of about 1.68 cc/g to about 2.19 cc/g.

19. A dual filter apparatus according to claim 17, wherein the apparent density of the carbon cores is about 0.19 g/cc to about 0.2 g/cc.

20. A dual filter apparatus according to claim 17, wherein the hemocompatible polymer coated carbon cores are coated with a semipermeable polymer coating comprising a methacrylate selected from the group consisting of polymethylmethacrylate (PMMA), polyethylmethacrylate (PEMA), polyhydroxyethyl-methacrylate (PHEMA) and combinations thereof.

* * * * *